United States Patent [19]

Kraus et al.

[11] Patent Number: 5,629,441
[45] Date of Patent: May 13, 1997

[54] 2-(ARYLIMINO-METHYL)-3-DIALKYLAMINOACRYLONITRILES, A PROCESS FOR THEIR PREPARATION AND THEIR USE

[75] Inventors: Helmut Kraus; Horst Behre, both of Odenthal; Helmut Fiege, Leverkusen, all of Germany

[73] Assignee: Bayer Aktiengesellschaft, Leverkusen, Germany

[21] Appl. No.: 514,277

[22] Filed: Aug. 11, 1995

[30] Foreign Application Priority Data

Aug. 19, 1994 [DE] Germany .................. 44 29 464.6

[51] Int. Cl.$^6$ .................................. C07C 255/00
[52] U.S. Cl. .......................... 558/357; 558/391
[58] Field of Search .................. 558/357, 391

[56] References Cited

U.S. PATENT DOCUMENTS

| | | | |
|---|---|---|---|
| 3,708,515 | 1/1973 | Thoma et al. | 260/464 |
| 4,319,024 | 3/1982 | Peeters et al. | 542/413 |
| 5,446,192 | 8/1995 | Kraus et al. | 560/172 |

OTHER PUBLICATIONS

M. Jachak, et al., Heterocycles, vol. 36, No. 10, pp. 2281–2290, (1993).
F.C. Uhle, et al., Journal of Organic Chemistry, vol. 10, pp. 76–86, (1945).
Chemical Abstracts, vol. 105, abstract No. 105: 208917y, abstract of JP 61-83,168, pp. 599–600, (1986).
Chemical Abstracts, vol. 105, abstract No. 105: 24275f, abstract of JP 61-30,576, p. 643, (1986).
M. Jachak, et al., Monatshefte für Chemie, vol. 124, pp. 199–207, (1993).
R. Benoit, et al., Synthesis, pp. 1124–1126, (1987).
H.-J. Sturm, et al., Liebigs Ann. Chem., vol. 729, pp. 139–145, (1969).
R.F. Abdulla, et al., Tetrahedron, vol. 35, pp. 1675–1735, (1979).

*Primary Examiner*—Johann Richter
*Assistant Examiner*—Ebenezer Sackey
*Attorney, Agent, or Firm*—Sprung Horn Kramer & Woods

[57] ABSTRACT 2-(Arylimino-methyl)-3-dialkylaminoacrylonitriles can be obtained by reaction of β-anilino-acrylonitriles with ortho-formamides. They are suitable as starting substances for the preparation of 4-amino-5-iminiummethylene-2-pyrimidines or 4-amino-5-formyl-2-pyrimidines.

7 Claims, No Drawings

2-(ARYLIMINO-METHYL)-3-DIALKYLAMINOACRYLONITRILES, A PROCESS FOR THEIR PREPARATION AND THEIR USE

The invention relates to 2-(arylimino-methyl)-3dialkylamino-acrylonitriles, a process for their preparation by reaction of β-anilinoacrylonitriles with orthoformic acid amides and their use for the preparation of 4-amino-5-iminiummethylene-2-pyrimidines or 4-amino-5-formly-2-pyrimidines.

As cyanomalonodialdehyde derivatives, 2-(arylimino-methyl)-3-dialkylamino-acrylonitriles are important components for the preparation of various heterocyclic compounds. It is thus possible to obtain from these intermediate products, for example, formyl- and cyanopyrimidines (JP 84-201 804 and JP 84-152 096), cyanopyrazoles (Mh. Chem. 124(1993), 199) and cyanopyridines (Synthesis 1987, 1124). 4-Amino-5-formyl-2-methylpyrimidine, which is an industrially important precursor of 4-amino-5-aminomethyl-2-methylpyrimidine ("Grewe-diamine", intermediate prodcut for the preparation of vitamin B1), is particularly important.

The invention thus relates to a process for the preparation of compounds of the formula

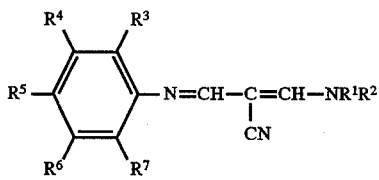

wherein
- $R^1$ and $R^2$ independently of one another denote linear or branched $C_1$–$C_8$-alkyl, $C_2$–$C_8$-alkenyl, $C_2$–$C_8$-alkoxyalkyl, $C_3$–$C_8$-alkoxyalkenyl, $C_3$–$C_8$-cycloalkyl, $C_7$–$C_{10}$-aralkyl, $C_6$–$C_{12}$-aryl or heterocyclic ring having 1 or 2 heteroatoms from the series consisting of N, O and S, or
- $R^1$ and $R^2$, together with the nitrogen atom on which they are located, denote a 5- to 8-membered ring which can contain a further heteroatom from the series consisting of N, O and S and
- $R^3$ to $R^7$ independently of one another denote linear or branched $C_1$–$C_8$-alkyl, $C_1$–$C_6$-alkoxy, $C_1$–$C_6$-alkylthio, $C_2$–$C_8$-alkenyl, $C_2$–$C_8$-alkoxyalkyl, $C_3$–$C_8$-cycloalkyl, halogen, di-$C_1$–$C_6$-alkylamino or, preferably, hydrogen, by reaction of compounds of the formula

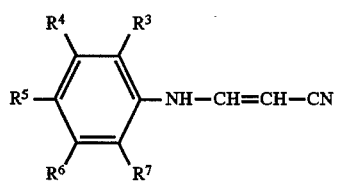

wherein
$R^3$ to $R^7$ have the above meaning,
with compounds of the formula

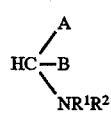

wherein $R^1$ and $R^2$ have the above meaning and
A and B independently of one another denote $OR^8$, $OR^9$, $NR^{10}R^{11}$ or $NR^{12}R^{13}$, wherein the substituents $R^8$ to $R^{13}$ independently of one another have the meaning defined above for $R^1$ and $R^2$, in a molar ratio of II/III of 0.5 to 20, preferably 0.8 to 5, in particular 1 to 3, at a temperature of 0° to 200° C., preferably 20° to 150° C.

The presure depends on the reaction temperature and on the nature of the compound III, in particular on the boiling point of the products HA and HB, and can be 0.1 to 20, preferably 1 to 5 bar.

The accessibility of the compound I by the process according to the invention is extremely surprising. In fact, reaction products of aniline and acetaldehyde exist not in the form 1 but in the form 2

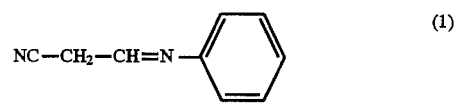

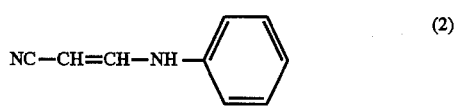

(M. Jachak et al., Monatshefte für Chemie 124, 199 (1993) in association with H.-J. Sturm et al., Liebigs Ann. Chem. 729, 139 (1969)). Accordingly, it would have to have been expected that alkylation o the nitrogen should take place during the reaction with compound III;, R. F. Abdulla et al., Tetrahedron 35, 1675 et seq. (1979).

Linear and branched $C_1$–$C_8$-alkyl includes, for example, methyl, ethyl, propyl, isopropyl, butyl, isobutyl, tert-butyl and one of the isomeric pentyls, hexyls or octyls, preferably the $C_1$–$C_4$-alkyl radicals mentioned.

Linear or branched $C_2$–$C_8$-alkenyl includes, for example, vinyl, propenyl, allyl or one of the isomeric butenyls, pentenyls, hexenyls or octenyls, preferably the $C_3$–$C_4$-alkenyl radicals mentioned.

Linear or branched $C_2$–$C_8$-alkoxyalkyl includes, for example, methoxymethyl, ethoxymethyl and other radicals from the group consisting of $C_3$–$C_9$-alkyl in whch a $CH_2$ group is replaced by an O atom.

Linear or branched $C_3$–$C_8$-alkoxyalkenyl includes, for example, methoxyvinyl, ethoxyvinyl, methoxyallyl, 2-methoxy-propenyl and other radicals from the group consisting of $C_4$–$C_9$-alkenyl wherein a $CH_2$ group is replaced by an O atom.

$C_3$-$C_8$-acycloalkyl includes, for example, cyclopropyl, methylcyclopropyl, dimethylcyclopropyl, cyclobutyl, methylcyclobutyl, cyclopentyl, methylcyclopentyl, cyclohexyl, methyl-cyclohexyl, dimethyl-cyclohexyl, cycloheptyl and cyclooctyl, preferably cyclopropyl and cyclohexyl, and methyl and dimethyl derivatives thereof.

$C_7$–$C_{10}$-Aralkyl includes, for example, 1-phenylethyl, 2-phenylethyl and preferably benzyl.

5- to 8-Membered saturated or unsaturated heterocyclic rings having 1 to 2 heteroatoms from the group consisting of N, O and S which may be mentioned are: pyrrole, furan, thiophene, pyrrolidine, pyrroline, pyrazole, imidazole, thiazole, oxazole, pyridine, pyrimidine, piperazine, morpholine, pyran, azepine, azocine, isoxazole, isoxazole, isothiazole, pyridazine and pyrazine, which can be substituted on the N atom by $C_1$–$C_4$-alkyl or by hydroxy-$C_1$–$C_4$-alkyl. The heterocyclic rings morpholine, pyrrolidine and piperidine, which can be substituted by $C_1$–$C_4$-alkyl or by hydroxy-$C_1$–$C_4$-alkyl, are particularly preferred.

$R^1$ and $R^2$ independently of one another preferably denote linear or branched $C_1$–$C_8$-alkyl, cyclopropyl, cyclopently, cyclohexyl, phenyl or benzyl or, together with the nitrogen atom on which they are located, a 5- or 6-membered ring which can contain a further heteroatom from the series consisting of N, O and S.

$R^1$ and $R^2$ independently of one another particularly denote linear or branched $C_1$–$C_4$-alkyl or, together with the nitrogen atom on which they are located, morpholine, pyrrolidine or piperidine, which can be substituted by $C_1$–$C_4$-alkyl or hydroxy-$C_1$–$C_4$-alkyl.

The starting materials II, such as, for example, 3-phenylaminoacrylonitrile, can be prepared, for example, from aniline, 3-ethoxyacrylonitrile and ammonia in accordance with EP-A 18 473 or in an analogous manner.

Dialkylaminoacrylonitriles, which are easily accessible industrially in a virtually quantitative yield, for example analogously to EP-A-560 158, can arylamines with the addition of acid to give the starting materials II.

The starting materials III include dimethylformamide acetals, aminal esters and triaminomethanes of the formulae

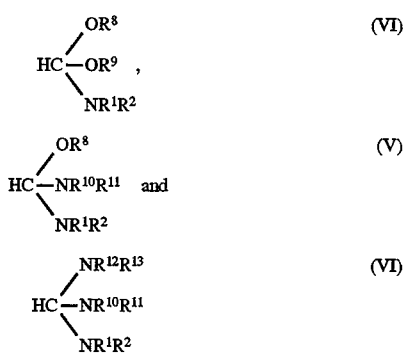

The reactions according to the invention can be illustrated by way of example as follows:

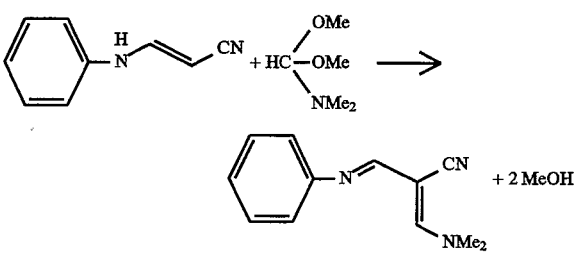

The process according to the invention can be carried out in the presence or absence of an organic solvent. Preferred organic solvents are aprotic and polar solvents, for example N-persubstituted acid amides, such as dimethylformamide (DMF), dimethylacetamide (DMAC), diethylacetamide and homologues thereof, N-methyl-pyrrolidone (NMP), N-methyl-caprolactam (NMC), phosphoric acid hexamethyl-triamide, tetramethyl-urea and the like, the group consisting of sulpholane and its derivatives substituted by methyl, ethyl and other inert substituents, the group consisting of sulphoxides, such as dimethyl sulphoxide, diethyl sulphoxide and others, and the group consisting of sulphones, such as diethyl sulphone, dimethyl sulphone and others. Since o-amides also have a polar aprotic character, it is possible to employ an excess of the compounds III as solvents and diluents endogenous to the system. It is even possible to dispense entirely with aprotic polar solvents which are foreign to the system. In the case where a foreign solvent is employed, N-persubstituted acid amides, specifically NMP, NMC, DMF or tetramethyl-urea, are especially preferred.

The progress of the reaction can be monitored, for example, by thin layer chromatography. When the reaction has ended, the solvent (if present) and the (usually) readily volatile alcohols and amines HA and HB can be stripped off. Since the reaction proceeds very selectively, the crude product often already has a purity of more than 95% and can thus, for example, be used directly for synthesis of heterocyclic compounds.

The invention also relates to the compounds I and their use for the preparation of 4-amino-5iminiummethylene-2-pyrimidines or 4-amino-5-formly-2-pyrimidines. For this purpose, the compounds I can be reacted with $C_1$–$C_6$-amidines at elevated temperature, for example at 60° to 150° C., to give the 4-amino-5-iminiummethylene-2-pyrimidines, from which the corresponding 5-formyl compounds are formed by hydrolysis in the case of aqueous working up.

The percentage data of the following examples in each case relate to the weight.

EXAMPLES

Example 1

29 g of trans-3-ethoxyacrylonitrile, 20.5 g of ammonia, 21 g of aniline and 10 ml of ethanol were stirred in a 0.31 V4A autoclave at 1000° C. for 4 hurs. After the ethanol had been distilled off, 200 ml of water were added and the mixture was extracted 3 times with 100 ml of diethyl ether. The 33 g of residue obtained after concentration were recrystallized from chloroform, which gave 15.2 g of trans-3-phenylaminoacrylonitrile. The product was identified by GC/MS analysis and comparison of the NMR data with that from EP-A 18 473.

$^1$H NMR (d-DMSO): 4.60 ppm (d,1H); 6.9–7.3 (m,5H); 7.85 (dd, 1H); 9.70 (d,1H)

Example 2

405 g of acetonitrile and 913 g of 89.6% pure ethoxy-bis(dimethylamino)methane (remainder DMF) were heated in a 31 V4A steel autoclave at 140° C. for 12 hours. After distillation, 3-dimethylaminoacrylonitrile was obtained as 98.8% pure product yield of 96.7% of theroy.

29 g of 3-dimethylaminoacrylonitrile, 28 g of aniline and 20 g of glacial acetic acid were stirred in 100 ml of dichloroethane at room temperature for 17 hours.

Water was then added in a volume ratio of 1:1, the phases were separated and the aqueous phase was extracted with dichloroethane. After the combined organic media had been concentrated, 40 g of crude product were obtained, which slowly crystallized completely.

According to $^1$H NMR, 90% of trans-3-phenylaminoacrylonitrile, 5% of the cis compound and 3% of dimethylaminomethyleneglutaconic acid dinitrile were present $^1$H NMR of the cis compound (d-DMSO): 4.27 ppm (d, 1H); 7.50 (dd, 1H); 6.9–7.3 (m, 5H), 9.52 ppm (d, 1H)

Example 3

14.4 g of trans-3-phenylaminoacrylonitrile, 20 ml of 82% pure DMF dimethyl acetal (contained DMF and methanol) and 150 ml of DMF where boiled under reflux for 2 hours. After the mixture had been concentrated on a rotary evaporator, 20.0 g of 97.8% pure 3-phenylimino-2-dimethylaminopropene-2-nitrile were obtained, corresponding to 98.3% of theory.

$^1$H NMR (d-DMSO: 3.18 and 3.31 ppm (broad s, each 3H, NMe$_2$); 6.95–7.10 and 7.25–7.35 (m, 5H, phenyl), 7.60 (s, 1H).

We claim:

1. A process for the preparation of a compound of the formula

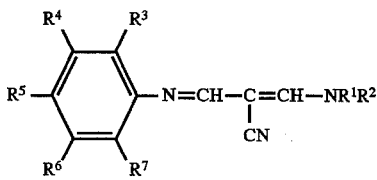 (I)

wherein

R$^1$ and R$^2$ independently of one another denote linear or branched C$_1$–C$_8$-alkyl, C$_2$–C$_8$-alkenyl, C$_2$14 C$_8$-alkoxyalkyl, C$_3$–C$_8$-alkoxyalkenyl, C$_3$–C$_8$-cycloalkyl, C$_7$–C$_{10}$-aralkyl, C$_6$–C$_{12}$-aryl or a 5- to 8-membered saturated or unsaturated heterocyclic ring having 1 to 2 heteroatoms from the series consisting of N, O and S, or R$^1$ and R$^2$, together with the nitrogen atom on which they are located, denote a 5- to 8-membered ring which may contain a further heteroatom from the series consisting of N, O and S and R$^3$ to R$^7$ independently of one another denote hydrogen, linear or branched C$_1$–C$_8$-alkyl, C$_1$–C$_6$-alkoxy, C$_1$–C$_6$-alkylthio, C$_2$–C$_6$-alkenyl, C$_2$–C$_6$-alkoxyalkyl, C$_3$–C$_8$-cycloalkyl, halogen, or di-C$_1$–C$_6$-alkylamino, by the reaction of a compound of the formula

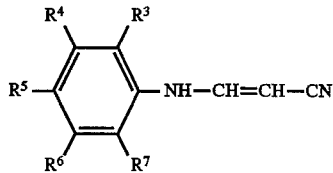 (II)

wherein

R$^3$ and R$^7$ have the above meaning, with a compound of the formula

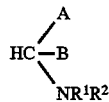 (III)

wherein

R$^1$ and R$^2$ have the above meaning and

A and B independently of one another denote OR$^8$, OR$^9$, NR$^{10}$R$^{11}$ or NR$^{12}$R$^{13}$, wherein the substituents R$^8$ to R$^{13}$ independently of one another have the meaning defined above for R$^1$ and R$^2$, in a molar ratio of II/III of 0.5 to 20, at a temperature of 0° to 200° C.

2. The process according to claim 1 wherein the molar ratio of compounds II and III is 0.8 to 5.

3. The process according to claim 1 by reaction of the compounds II and III in a molar ratio of 1 to 3.

4. The process according to claim 1 wherein the reaction temperature is from 20° to 150° C.

5. A compound of the formula

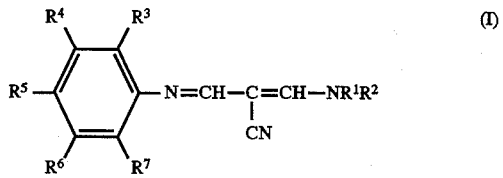 (I)

wherein

R$^1$ and R$^2$ independently of one another denote linear or branched C$_1$–C$_8$-alkyl, C$_2$–C$_8$-alkenyl, C$_2$–C$_8$-alkoxyalkyl, C$_3$–C$_8$-alkoxyalkenyl, C$_3$–C$_8$-cycloalkyl, C$_7$–C$_{10}$-aralkyl, C$_6$–C$_{12}$-aryl or a 5- to 8-membered saturated or unsaturated heterocyclic ring having 1 to 2 heteroatoms from the series consisting of N, O and S, or R$^1$ and R$^2$, together with the nitrogen atom on which they are located, denote a 5- to 8-membered ring which may contain a further heteroatom from the series consisting of N, O and S and R$^3$ to R$^7$ independently of one another denote hydrogen, linear or branched C$_1$–C$_8$-alkyl, C$_1$–C$_6$-alkoxy, C$_1$–C$_6$-alkylthio, C$_2$–C$_8$-alkenyl, C$_2$–C$_8$-alkoxyalkyl, C$_3$–C$_6$-cycloalkyl, halogen, or di-C$_1$–C$_6$-alkylamino.

6. A compound according to claim 5, wherein R$^3$ to R$^7$ are hydrogen.

7. A compound according to claim 5, wherein the compound is 3-phenylimino-2-dimethylpropene-2-nitrile.

* * * * *

UNITED STATES PATENT AND TRADEMARK OFFICE
CERTIFICATE OF CORRECTION

PATENT NO. : 5,629,441
DATED : May 13 1997
INVENTOR(S) : Kraus, et al.

It is certified that error appears in the above-indentified patent and that said Letters Patent is hereby corrected as shown below:

Col. 5, line 14    Delete " $C_2 14$ " and substitute -- $C_2$- --

Col. 5, line 18    After " 1 " delete " to " and substitute -- or --

Col. 5, line 26    Delete " $C_2$-$C_6$-alkenyl, $C_2$-$C_6$-alkoxyalkyl " and substitute -- $C_2$-$C_8$-alkenyl, $C_2$-$C_8$-alkoxyalkyl --

Col. 6, line 29
(Pg. 4, line 4    After " 1 " delete " to " and substitute -- or --

Col. 6, lines 39-40    Delete " $C_3$-$C_6$-cycloalkyl " and substitute -- $C_3$-$C_8$-cycloalkyl --

Signed and Sealed this

Thirteenth Day of January, 1998

Attest:

BRUCE LEHMAN

Attesting Officer            Commissioner of Patents and Trademarks